United States Patent [19]

Kim et al.

[11] Patent Number: 5,227,141
[45] Date of Patent: Jul. 13, 1993

[54] MEMBRANE CATALYTIC REACTOR COMPRISING HETEROPOLYACID CATALYST AND POLYSULFONE MEMBRANE

[75] Inventors: Jae J. Kim; Wha Y. Lee; In K. Song, all of Seoul, Rep. of Korea

[73] Assignee: Korea Institute of Science and Technology, Seoul, Rep. of Korea

[21] Appl. No.: 878,531

[22] Filed: May 5, 1992

[30] Foreign Application Priority Data

Aug. 12, 1991 [KR] Rep. of Korea .................... 91-13858

[51] Int. Cl.$^5$ ...................... B01J 8/02; B01D 15/04; C07C 41/00
[52] U.S. Cl. .................................... 422/211; 422/221; 422/238; 210/638; 210/640; 210/500.41; 568/698
[58] Field of Search ............... 422/211, 213, 221, 311, 422/130, 238, 239; 210/638, 640, 500.41; 568/698

[56] References Cited

U.S. PATENT DOCUMENTS

| | | | |
|---|---|---|---|
| 4,754,089 | 6/1988 | Matson et al. | 570/260 |
| 4,827,048 | 5/1989 | Knifton | 568/698 |
| 4,938,931 | 7/1990 | Cussler | 422/211 |
| 5,045,205 | 9/1991 | Taylor | 210/638 |
| 5,106,502 | 4/1992 | Goldsmith | 210/490 |
| 5,124,041 | 6/1992 | Sheer et al. | 210/641 |

OTHER PUBLICATIONS

Chemistry Letters, pp. 1335–1338, 1990, S. Uemiya, et al., "Aromatization of Propane Assisted by Palladium Membrane Reactor".

Applied Catalysis, vol. 67, pp. 223–230, 1991, S. Uemiya, et al., "Steam Reforming of Methane in a Hydrogen-Permeable Membrane Reactor".

Ind. Eng. Chem. Prod. Res. Develop., vol. 13, No. 4, pp. 267–274, 1974, G. A. Tsigdinos, "Preparation and Characterization of 12-Molybdophosphoric and 12-Molybdosilicic Acids and their Metal Salts".

Primary Examiner—Robert J. Warden
Assistant Examiner—Christopher Y. Kim
Attorney, Agent, or Firm—Oblon, Spivak, McClelland, Maier & Neustadt

[57] ABSTRACT

A membrane catalytic reactor which comprises a heteropolyacid selected from the group consisting of 12-tungstophosphoric acid, 12-molybdophosphoric acid, 12-molybdotungstophosphoric acid, and 12-tungstosilicic acid, and polysulfone membrane is provided. This membrane catalytic reactor is applicable to vapor-phase dehydration, dehydrogenation, oxidation, and simultaneous separation of organic or inorganic materials, particularly vapor-phase dehydration of ethanol.

2 Claims, 3 Drawing Sheets

MEMBRANE CATALYTIC REACTOR COMPRISING HETEROPOLYACID CATALYST AND POLYSULFONE MEMBRANE

BACKGROUND OF THE INVENTION

1. Field of the Invention

The present invention relates to an improvement in the fixed bed reactors which are commonly used in fundamental chemical processes. More particularly, the invention relates to a membrane catalytic reactor in which the reaction and separation are carried out simultaneously in a single step resulting in an improvement in reaction productivity and separation efficiency.

2. Description of the Prior Art

In conventional chemical processes using a fixed bed reactor, a reaction and a separation steps are independently carried out. Generally, it is essential to carry out the separation step in order to recover the final product formed from the reaction in desired purity.

In general, most chemical reactions occur at a high temperature over 300° C. At such an elevated temperature, polymeric separation membranes exhibit thermal instability; thus, few polymeric separation membranes have been used for membrane catalytic reactors. Consequently, nowadays, studies on inorganic membranes which can endure high temperatures have extensively been performed.

For example, Uemiya, et al. used a palladium catalyst membrane reactor in the aromatization of propane; see Chemistry Letters, pp. 1335-1338 (1990). Uemiya, et al. also used a hydrogen-permeable membrane in the steam reforming of methane; see Applied Catalysis, 67, pp. 223-230 (1991).

However, the separation mechanism of these inorganic membranes generally exhibits characteristics depending on their pore sizes and, thus, the mechanism is simpler than that of polymeric separation membranes. Therefore, the inorganic membrane cannot afford a variety of characteristics of separating materials.

Polymeric separation membranes have low thermal stability. However, the separation mechanism of these membranes varies with the diffusibility and the solubility of the relevant material; thus, they can have good separation abilities for a variety of materials in chemical reactions at low temperatures.

SUMMARY OF THE INVENTION

An object of the invention is to provide a membrane catalytic reactor having an improved separation ability.

Another object of the invention is to provide a membrane catalytic reactor which is widely applicable to a process for vapor-phase dehydration, dehydrogenation, oxidation, or simultaneous separation of organic or inorganic materials, especially a process for the production of ethylene by vapor-phase dehydration of ethanol at temperatures of below 150° C.

These and other objects of the invention can be achieved by the membrane catalytic reactor according to the present invention, comprising:

a first disc-like plate having a sample inlet at its center;

a catalyst bed;

a catalyst bed support located under the first plate and having a truncated cone-shaped hole suitable for fixing the catalyst bed at its center and for guiding a flow of a sample towards the center;

a second disc-like plate located under the catalyst bed support to maintain the support in fixation and having a buffer zone at its center and an outlet for evacuating discharged materials on its side;

a polysulfone membrane located under the second plate;

a polysulfone membrane support, the support being so porous that the gases permeated through the membrane can freely pass;

a set of thermocouples located between the upper of the membrane and the catalyst bed for sensing and controlling a temperature of the reactor;

a third plate forming the base of the reactor to keep said polysulfone membrane fixed and having an outlet at its center for evacuating the gaseous materials which have permeated through the polysulfone membrane; and O-ring seals inserted between the first plate and the catalyst bed support, the catalyst support and the second plate, the second plate and the polysulfone membrane, and the polysulfone membrane support and the third plate.

BRIEF DESCRIPTION OF THE DRAWINGS

The present invention will be described in greater detail with reference to the accompanying drawings wherein.

DETAILED DESCRIPTION OF THE INVENTION

According to the present invention, the reactor is mainly constructed with three disc-like plates. A disc-like catalyst support, for fixing a catalyst bed, made of a heat resistant material, for example, TEFRON, is inserted between the first and the second plates. A truncated cone-shaped hole present at the center of the catalyst support is filled with a heteropolyacid catalyst as a fixed bed. Also, a polysulfone membrane support, in which a number of holes are perforated so that the gases permeated through the membrane can readily pass through the holes without any resistance, is installed to prevent any damages to the polysulfone membrane owing to partial overheating between the second and the third plates.

The heteropolyacid useful for the invention may include 12-tungstophosphoric acid ($H_3PW_{12}O_{40}$), 12-molybdophosphoric acid ($H_3PMo_{12}O_{40}$), 12-molybdotungstophosphoric acid ($H_3PMo_xW_{12-x}O_{40}$) and 12-tungstosilicic acid ($H_4SiW_{12}O_{40}$), which are prepared by the Tsigdinos's method; see Ind. Eng. Chem. Prod. Res. Dev., 13(6), pp. 267 (1974).

The polysulfone membrane is prepared taking into account the solubility of polysulfone in a number of solvents. Polysulfone is very well soluble in dimethylformamide, dimethylacetamide, cyclohexanone, tetrahydrofuran, chlorobenzene, chloroform, etc. In the present invention, the polysulfone membrane is prepared by dissolving 25-30 percent by weight of polysulfone in 70-75 percent by weight of dimethylformamide, and spreading the resulting solution on a flat glass plate followed by drying in air to give a flat polysulfone membrane. The resulting flat polysulfone membrane of 17.65 cm² in area and 0.266 mm in thickness is used in an embodiment of the membrane catalytic reactor according to the present invention. Thermodegradation temperature at which the heteropolyacids lose their catalytic ability is above 400° C. Glass transition temperature of the polysulfone membrane is about 195° C., and, thus, the catalyst and the membrane are thermally stable under reaction temperatures of below 150° C.

Now, hereinafter, the present invention will be described in greater detail with reference to the drawings.

Figure 1:
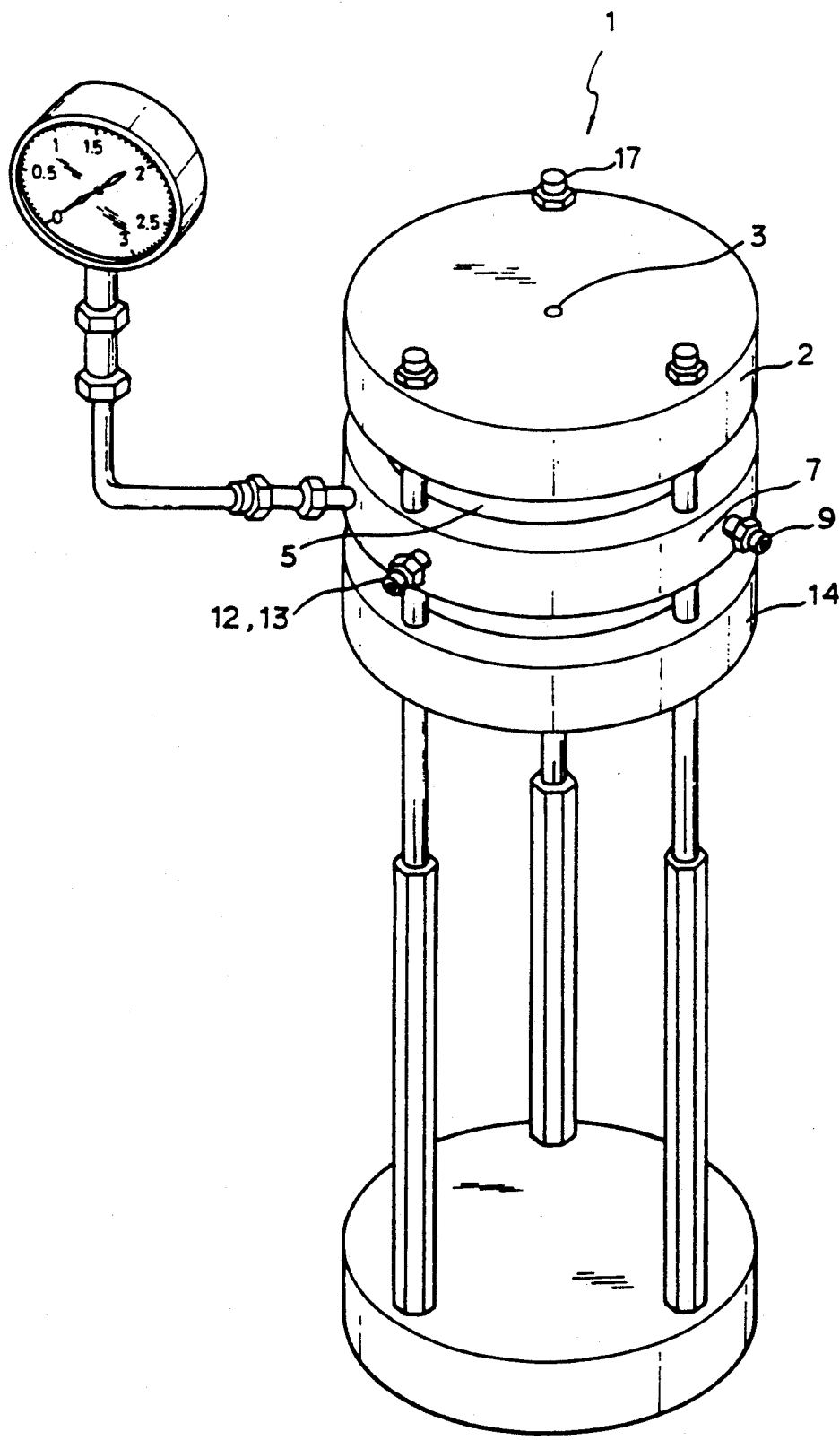
FIG. 1 is a perspective view of an embodiment of the membrane catalytic reactor according to the invention.
Figure 2:
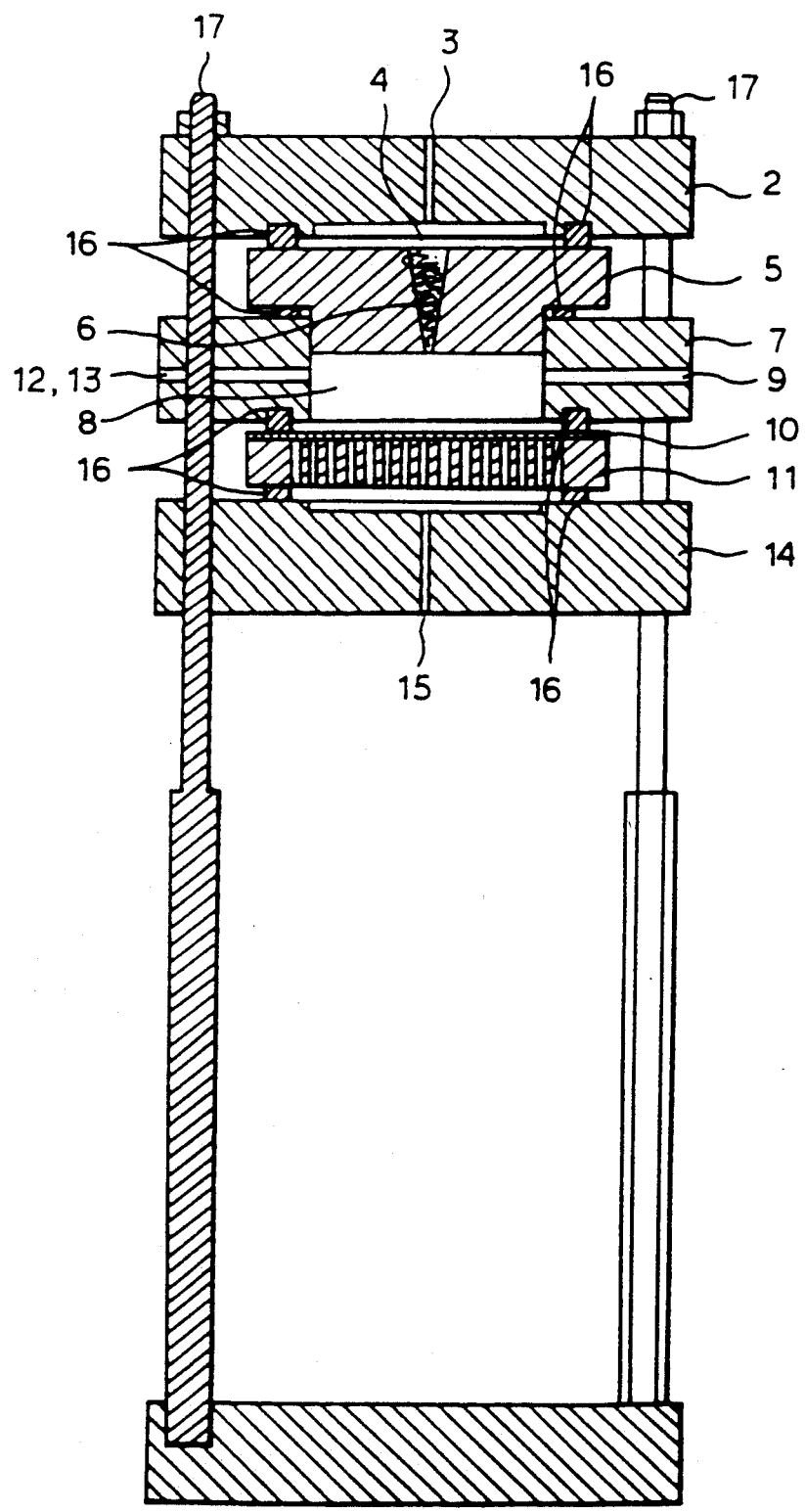
FIG. 2 is a sectional view of the membrane catalytic reactor, as shown in FIG. 1, according to the invention.

Referring to FIGS. 1 and 2 illustrates a membrane catalytic reactor 1 according to the present invention. This reactor is designed so as to reduce any damages to the polysulfone membrane due to local overheating of the membrane catalytic reactor. The reactor 1 is constructed of a first disc-like plate 2 having a sample inlet 3 at its center; a catalyst bed 4; a catalyst bed support 5 located under the plate 2 and having a truncated cone-shaped hole 6 suitable for fixing the bed 4 at its center and for guiding a flow of a sample to the center; a second plate 7 located under the catalyst bed support 5 to maintain the support 5 in fixation and having a buffer zone 8 at its center and an outlet 9 on its side for evacuating the materials being discharged; a polysulfone membrane 10 located under the second plate 7; a polysulfone membrane support 11 positioned under the polysulfone membrane 10; a set of thermocouples 12 and 13 provided between the catalyst bed 4 and the upper of the membrane 10 for sensing and controlling temperatures of said reactor 1; a third plate 14 forming the base of the reactor 1 to maintain the polysulfone membrane 10 in fixation and having an outlet 15 at its center for evacuating the materials which have permeated through the membrane 10; and O-ring seals 16 inserted between each of the first plate 2 and the catalyst bed support 5, the support 5 and the second plate 7, the plate 7 and the polysulfone membrane 10, and the polysulfone membrane support 11 and the third plate 14 in order to provide the reactor 1 with tight seal conditions. The plates 2, 7 and 14 are entirely fixed to the reactor 1 by means of bolts and nuts 17.

Figure 3:
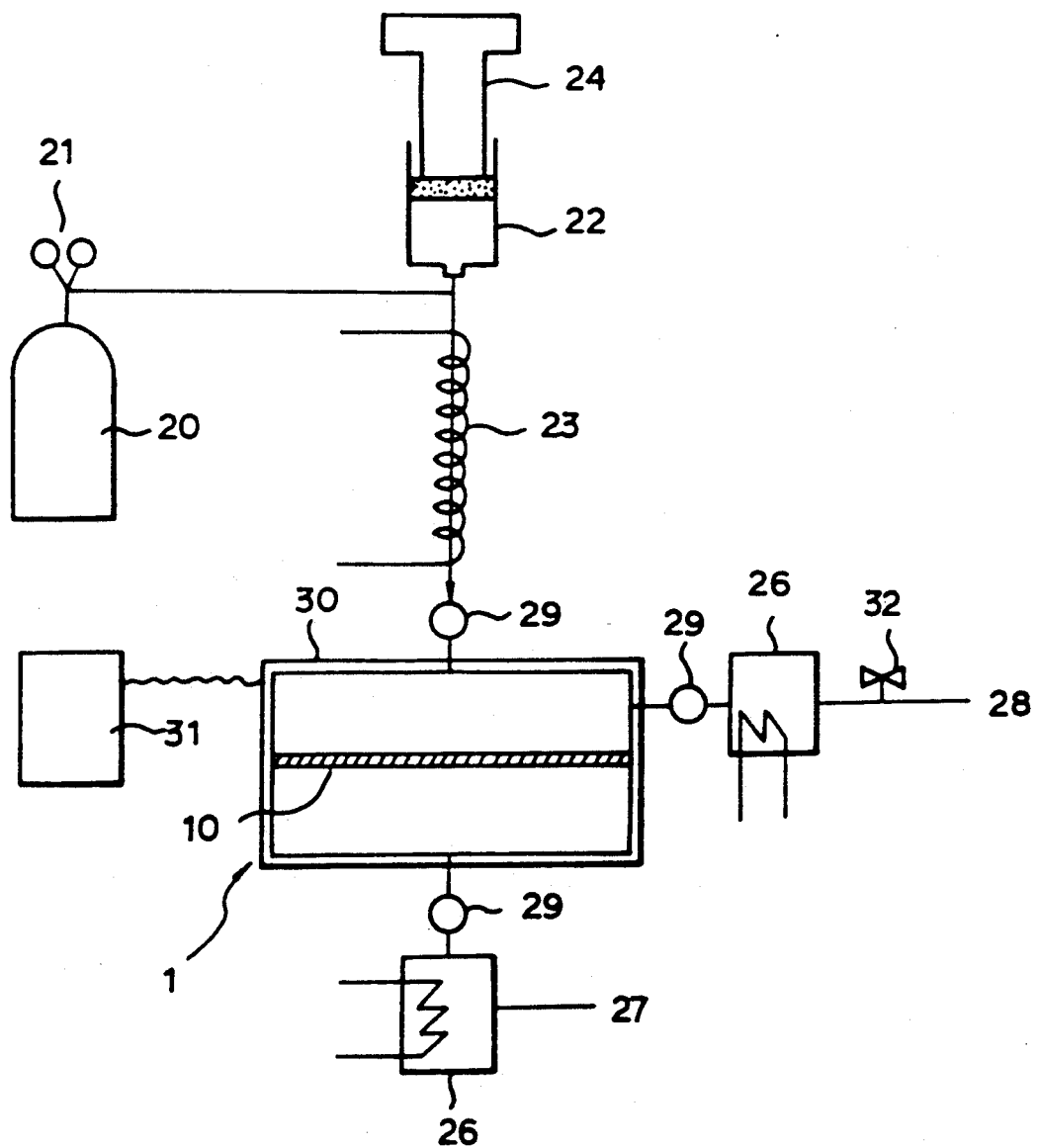
FIG. 3 is a flow diagram showing a dehydration reaction of ethanol using the membrane catalytic reactor according to the invention.

FIG. 3 shows a flow diagram of a dehydration reaction of ethanol using the membrane catalytic reactor 1 according to the invention. Helium contained in a helium reservoir 20 is introduced as a carrier gas into the reactor 1 via a pressure regulator 21 at a flow rate of 3 ml per minute. Liquid ethanol contained in an ethanol reservoir 22 is introduced via a preheating zone 23 which is maintained at 100° C. into the reactor 1 with a carrier gas, e.g., helium, by an ethanol injector 24. The vapor-phase ethanol thus introduced is subject to chemical reaction while passing through the catalyst bed 4 in which a heteropolyacid is contained as a fixed bed. Diethyl ether and ethylene thus produced by the chemical reaction and unreacted ethanol are present at the buffer zone 8. These products exhibit various permeabilities through the polysulfone membrane 10.

The materials which have permeated through the polysulfone membrane 10 permeate in turn through the porous support 11 supporting the membrane 10, while part of the products which cannot permeate through the membrane 10 and thus which are present in the buffer zone s are successively evacuated through the outlet 9. A permeation ratio, that is, the rate of permeation/introduction, can be adjusted by means of a microvalve 32. Through a condenser 26, the permeated and the evacuated materials 27 and 28 are discharged. Sample collecting holes 29 may be installed before and behind the membrane catalytic reactor 1 to analyze the distribution of the products at each position with a gas chromatography packed with PORAPAK Q.

A temperature of the membrane catalytic reactor 1 is generally regulated using a band heater 30 and a thermoregulator 31. A set of thermocouples 12 and 13 are also installed between the catalyst bed and the upper of the membrane to sense and control precisely the temperature of the membrane catalytic reactor 1.

DESCRIPTION OF THE PREFERRED EMBODIMENT

The invention will be further illustrated by way of the following examples. The examples are presented for illustrative purpose only and should not be construed as limiting the invention, which is properly delineated in the claims.

EXAMPLE 1

Permeation rate of pure materials through polysulfone membrane

The amount of material permeated through a membrane can be calculated according to the following equation:

$$J = p \frac{(A)(\Delta P)}{(d)}$$

wherein

J : amount of permeation in cm³/sec;
A : area of membrane in cm²;
$\Delta P$: pressure of permeated materials in cmHg;
d : thickness of membrane in cm; and
p : permeation rate in cm³-cm/cm²-sec-cmHg According to the above equation, the permeation rate of a material can be calculated when the thickness and the area of the membrane used, the pressure of the permeated materials, and the amount of the materials permeated are given.

Also, the permeation selectivity is defined as a relative ratio of the permeation rate for the respective materials. In the present example, ethanol was subject to dehydration reaction to obtain diethyl ether and ethylene as desired products, together with coexisting unreacted ethanol. The permeation rate and the permeation selectivity of each of pure diethyl ether, ethylene, and ethanol are set forth in Table 1 below.

TABLE 1

Permeation rate and permeation selectivity of pure materials through polysulfone membrane at various temperatures

| | Material | Temperature 130° C. | 140° C. | 150° C. |
|---|---|---|---|---|
| Permeation rate (cm³-cm/cm²-sec-cmHg) | ethylene | 2.043E-8 | 2.129E-8 | 2.702E-8 |
| | ethanol | 5.987E-9 | 6.084E-9 | 7.302E-9 |
| | diethyl ether | 3.207E-9 | 3.703E-9 | 3.945E-9 |
| Permeation selectivity | ethylene/ethanol | 3.42 | 3.50 | 3.70 |
| | ethanol/diethyl ether | 1.87 | 1.64 | 1.85 |

As can be seen from Table 1 above, the permeation rate of ethylene is greater than that of either ethanol or diethyl ether. Therefore, according to the membrane catalytic reactor of the invention using the polysulfone membrane, ethylene is selectively permeated through the polysulfone membrane, and thus, a larger amount of ethylene per unit time can be produced.

EXAMPLE 2

Conversion rate of ethanol and selectivities of products depending on reaction temperatures and catalytic reaction time In order to examine the efficiency and the performance for vapor-phase dehydration, dehydrogenation, and oxidation of the membrane catalytic reactor according to the invention consisting of a heteropolyacid and the polysulfone membrane, a dehydration reaction of ethanol was representatively carried out using both a conventional fixed bed reactor and a membrane catalytic reactor of the invention. The following comparative results are obtained.

The conversion rate of ethanol and the selectivity of the end product with respect to an input in each of the conventional fixed bed reactor and the membrane catalytic reactor according to the present invention were calculated based on the carbon number according to the following equation:

$$\text{Conversion rate (\%)} = \frac{\text{Total carbon number of ethylene and diethyl ether produced}}{\text{Carbon number of ethanol introduced into reactor}} \times 100$$

$$\text{Selectivity (\%)} = \frac{\text{Carbon number of ethylene or diethyl ether produced}}{\text{Total carbon number of ethylene and diethyl ether produced}} \times 100$$

The performance of both reactors depending on the reaction temperatures and the catalytic reaction time was also compared with each other. The results are as shown in Tables 2 and 3 below.

TABLE 2

Conversion rate of ethanol and selectivities of products depending on reaction temperatures

| Reaction temperature (°C.) | Conversion rate of ethanol (%) | | Selectivity (%) | | | |
|---|---|---|---|---|---|---|
| | | | ethylene | | diethyl ether | |
| | FBR[1] | MCR[2] | FBR | MCR | FBR | MCR |
| 130 | 10 | 17 | 1 | 19 | 99 | 81 |
| 135 | 13 | 24 | 1.5 | 22.7 | 98.5 | 77.3 |
| 140 | 23 | 33 | 2 | 29 | 98 | 71 |
| 145 | 33 | 44 | 5.3 | 40.8 | 94.7 | 59.2 |
| 150 | 40 | 50 | 9.3 | 66.5 | 90.7 | 33.5 |

Notes:
Catalytic reaction time: 37 g-catalyst-hr/ethanol mol
Catalyst: 12-tungstophosphoric acid ($H_3PW_{12}O_{40}$)
[1] FBR: fixed bed reactor
[2] MCR: membrane catalytic reactor

TABLE 3

Conversion rate of ethanol and selectivities of products depending on catalytic reaction time

| Catalytic reaction time* | Conversion rate of ethanol (%) | | Selectivity (%) | | | |
|---|---|---|---|---|---|---|
| | | | ethylene | | diethyl ether | |
| | FBR[1] | MCR[2] | FBR | MCR | FBR | MCR |
| 13.15 | 16 | 30 | 4.2 | 43.9 | 95.8 | 56.1 |
| 18.64 | 18 | 33 | 8.7 | 52.7 | 91.3 | 47.3 |
| 31.14 | 31 | 48 | 14.9 | 66.7 | 85.1 | 33.3 |
| 46.81 | 42 | 57 | 23.5 | 70.7 | 76.5 | 29.3 |
| 69.50 | 48 | 67 | 35 | 73.9 | 65 | 26.1 |

Notes:
Catalytic reaction temperature: 150° C.
Catalyst: 12-molybdophosphoric acid ($H_3PMo_{12}O_{40}$)
Catalytic reaction time*: g-catalyst-hr/ethanol mol
[1] FBR: fixed bed reactor
[2] MCR: membrane catalytic reactor As can be seen from Tables 2 and 3 above, under the same conditions, the conversion rate of ethanol and the selectivity of ethylene are higher in the catalyst membrane reactor according to the invention than in the conventional fixed bed reactor.

EXAMPLE 3

Materials balances relation at reaction temperature of 150° C.

Data for carbon material balances based on 100 mol of ethanol charged into a reactor at 150° C. are set forth in Table 4 below. In comparison of the fixed bed reactor with the membrane catalytic reactor according to the present invention under the same conditions, it can be seen that 11.1 mol (60-37.6-11.3) of ethanol and 15 mol (36.3-12.6-8.7) of diethyl ether were converted into 26.1 mol (25+4.8-3.7) of ethylene additionally by the action of the membrane catalytic reactor only. At the above reaction temperature, the fixed bed reactor produced a relatively large amount of diethyl ether as compared with ethylene. However, according to the membrane catalytic reactor, ethylene was able to easily permeated through polysulfone membrane while ethanol and diethyl ether did not permeate therethrough. The lesspermeated materials are retained in the buffer zone as shown in FIG. 2 over a long period of time during which they were readsorbed into the bulk of heteropolyacid, and then converted again into ethylene. This was attributed to the unique action of heteropolyacid. Therefore, it is believed that the superior performance of the membrane catalytic reactor according to the present invention is due to the specific catalytic action of heteropolyacid and the specific permeation properties of the polysulfone membrane for materials.

TABLE 4

Materials balances based on 100 mol of ethanol introduced at reaction temperature of 150° C.

| Fixed bed reactor | | | Membrane catalytic reactor | | | | | |
|---|---|---|---|---|---|---|---|---|
| | | | permeated portion | | | discharged portion | | |
| ETOH[1] | ETYN[2] | DIET[3] | ETOH | ETYN | DIET | ETOH | ETYN | DIET |
| 60 | 3.7 | 36.3 | 37.6 | 25 | 12.6 | 11.3 | 4.8 | 8.7 |

Notes:
Catalytic reaction time: 37 g-catalyst-hr/ethanol mol
Catalyst: 12-tungstosilicic acid ($H_4SiW_{12}O_{40}$)
[1] ETOH: ethanol;
[2] ETYN: ethylene;
[3] DIET: diethyl ether

What is claimed is:
1. A membrane catalytic reactor which comprises:
a first disc plate having a sample inlet at its center;
a catalyst bed;

a catalyst bed support located under and axially aligned with the first plate and having a tapered hole at its center containing the catalyst bed and for guiding a flow of sample through the tapered hole of said support;

a second disc plate located under and axially aligned with the catalyst bed support having a center hole to support said catalyst bed support in a fixed relationship and further defining a buffer zone, said second plate further having an outlet from the buffer zone to the atmosphere for evacuating discharged materials on its side;

a polysulfone membrane located under and axially aligned with the second plate;

a polysulfone membrane support located under and axially aligned with the polysulfone membrane for supporting said polysulfone membrane, the membrane support being porous so that the gases can permeate through the polysulfone membrane and said membrane support;

a set of thermocouples located between a top portion of the polysulfone membrane and the catalyst bed for sensing and controlling the temperature of the reactor;

a third disc plate located under and axially aligned under the membrane support forming the base of the reactor to keep the polysulfone membrane and the membrane support fixed and having an outlet at its center for evacuating the gaseous material which have permeated through the polysulfone membrane;

a first O-ring seal inserted between the first plate and the catalyst bed support;

a second O-ring seal inserted between the catalyst bed support and the second plate;

a third O-ring seal inserted between the second plate and the polysulfone membrane; and a fourth O-ring seal inserted between the polysulfone membrane support and the third plate.

2. The membrane catalytic reactor of claim 1, wherein said catalyst is a heteropolyacid selected from the group consisting of 12-tungstophosphoric acid, 12-molybdophosphoric acid, 12-molybdotungstophosphoric acid, and 12-tungstosilicic acid.

* * * * *